United States Patent
Smith et al.

(10) Patent No.: US 9,816,805 B2
(45) Date of Patent: Nov. 14, 2017

(54) COMPENSATION FOR GOOS-HANCHEN ERROR IN AUTOFOCUS SYSTEMS

(71) Applicant: Nikon Corporation, Tokyo (JP)

(72) Inventors: Daniel Gene Smith, Tucson, AZ (US); Eric Peter Goodwin, Tucson, AZ (US)

(73) Assignee: NIKON CORPORATION, Tokyo (JP)

( * ) Notice: Subject to any disclaimer, the term of this patent is extended or adjusted under 35 U.S.C. 154(b) by 585 days.

(21) Appl. No.: 14/302,187

(22) Filed: Jun. 11, 2014

(65) Prior Publication Data
US 2014/0293278 A1 Oct. 2, 2014

Related U.S. Application Data

(63) Continuation of application No. 12/884,890, filed on Sep. 17, 2010, now abandoned.
(Continued)

(51) Int. Cl.

| G01B 11/14 | (2006.01) |
|---|---|
| G01B 11/06 | (2006.01) |
| G02B 7/28 | (2006.01) |
| G01B 11/02 | (2006.01) |
| G01N 21/25 | (2006.01) |
| G02B 7/36 | (2006.01) |
| G01J 3/02 | (2006.01) |

(52) U.S. Cl.
CPC .............. *G01B 11/14* (2013.01); *G01B 11/02* (2013.01); *G01B 11/0608* (2013.01); *G01N 21/25* (2013.01); *G02B 7/28* (2013.01); *G01J 3/0237* (2013.01); *G01J 3/0297* (2013.01); *G02B 7/36* (2013.01)

(58) Field of Classification Search
CPC ..... G01B 11/14; G01B 11/02; G01B 11/0608; G01N 21/25; G01J 3/0237; G01J 3/0297; G02B 7/36
See application file for complete search history.

(56) References Cited

U.S. PATENT DOCUMENTS

| 7,248,337 B2 * | 7/2007 | Teunissen ............. G03F 9/7034 |
|---|---|---|
| | | 250/201.2 |
| 7,265,364 B2 | 9/2007 | Teunissen et al. |

(Continued)

FOREIGN PATENT DOCUMENTS

| EP | 1956339 A1 | 8/2008 |
|---|---|---|
| WO | 9939376 | 8/1999 |
| WO | 2007058151 A1 | 5/2007 |

OTHER PUBLICATIONS

Gonzalo R. Feijoo, et al., "A Computational Technique to Optimally Design In-Situ Diffractive Elements: Applications to Projection Lithography at the Resist Resolution Limit", Optical Microlithography XXII, Proc. of SPIE vol. 7274, 2009, pp. 1-16.

*Primary Examiner* — Kara E Geisel
*Assistant Examiner* — Rebecca C Bryant
(74) *Attorney, Agent, or Firm* — Yakov S. Sidorin; Quarles & Brady LLP (57) ABSTRACT

Method of predicting a distribution of light in an illumination pupil of an illumination system includes identifying component(s) of the illumination system the adjustment of which affects this distribution and simulating the distribution based on a point spread function defined in part by the identified components. The point spread function has functional relationship with configurable setting of the illumination settings.

22 Claims, 5 Drawing Sheets

Related U.S. Application Data

(60) Provisional application No. 61/244,321, filed on Sep. 21, 2009.

(56) References Cited

U.S. PATENT DOCUMENTS

| | | |
|---|---|---|
| 7,489,399 B1 | 2/2009 | Lee |
| 2004/0165169 A1 | 8/2004 | Teunissen et al. |
| 2006/0007429 A1 | 1/2006 | Emer et al. |
| 2008/0118886 A1* | 5/2008 | Liang .................. A61B 5/0066 433/29 |
| 2008/0279457 A1* | 11/2008 | Shioya .................. G01B 11/25 382/191 |
| 2009/0116039 A1 | 5/2009 | Hidaka |

* cited by examiner

COMPENSATION FOR GOOS-HANCHEN ERROR IN AUTOFOCUS SYSTEMS

RELATED APPLICATION/CLAIM OF PRIORITY

This application is a continuation from U.S. patent application Ser. No. 12/884,890 that has been published as U.S. 2011/0071784 and that claims priority from a provisional patent application Ser. No. 61/244,321, filed on Sep. 21, 2009, which provisional application is incorporated by reference herein.

BACKGROUND

The present invention provides a method for compensating errors due to the Goos-Hanchen effect in an autofocus (AF) system.

The Goos-Hanchen (GH) effect produces a shift of a beam when incident on an optical interface (e.g. a substrate that is imaged by an imaging optical system in the production of a semiconductor wafer). In one way of looking at this effect, any monochromatic beam incident on a reflecting surface can be decomposed into a sum of plane waves. The reflecting surface (e.g. the substrate surface) then produces a different phase for each plane wave depending on its angle of incidence. Very often, over a small range of angles, this phase on reflection will either increase or decrease with the angle of incidence producing a tilted wavefront in the far field, which is the same as a shifted spot at the reflecting surface—the near field. In an imaging optical system that includes a reflective surface near an image, this effect will produce a shift of the image. This is also true in an autofocus system that images some source object (e.g. a slit or fringes) onto the surface of investigation (e.g. a wafer) at a glancing angle of incidence and then relays that image to a detector. The position of the image on the detector will depend on the height of the surface of investigation, but will also depend on the variation of phase on reflection produced by that surface—the GH effect. In an AF system, this means that variations in the surface construction, which may consist of many thin film layers and printed circuit patterns, will produce an error in the surface height measurement; we call this the GH error.

The problem with the GH error is that it can vary with underlying substrate patterns, and coating thicknesses, and that variation can be large, e.g. several hundred nanometers to several microns. Moreover, that variation is typically indistinguishable from the substrate (substrate) topography in an optically based AF system.

One approach to compensating the GH-effect is to use ellipsometry to determine the substrate film structure, and then use the film structure to estimate the GH error, and finally subtract that error from the measured surface height. However, ellipsometry requires a complex optical system of its own, a big increase in computational power, and a lot of input from the user.

SUMMARY OF THE INVENTION

The present invention provides a method for compensating errors caused by the Goos-Hanchen effect in an optical autofocus system that uses the position of an image reflected from a substrate (e.g. wafer surface) to determine changes in the z position of the substrate. According to the invention, reflected light from the substrate is provided at a plurality of wavelengths and polarizations, detected and used to make corrections that compensate for the errors due to the Goos-Hanchen effect.

One way of compensating GH errors, according to the principles of the present invention, is referred to as the "analog" approach. In this approach, a broad band light spectrum is directed at the substrate, so that the variation of GH error is minimized across various substrate patterns. This approach is already deployed, in a non-optimized way, in very broadband AF systems, where the influence of spectrally isolated GH errors are reduced by the more ubiquitous spectral components that have smaller GH errors. However, according to the present invention, the broad band illuminating spectrum is filtered, e.g. with a dynamic filter, or with a custom interference filter before reaching the detector so that the average GH error (averaged across wavelength and polarization by the detector) is minimized. This key idea behind this approach is that the GH error is an average over the spectrum and polarizations and that no further specialized data processing is necessarily used in correcting the GH error. We therefore call it the "analog approach".

Another embodiment comprises a slight modification to the analog approach. In this case the position of the imaged source object, each wavelength, or wavelength band, and/or polarization receives a shift that biases the measured substrate position for that wavelength, wavelength band and/or polarization so that the average position is further compensated for GH errors. Such a bias could be achieved in a fringe projection system using a modified spectral filter that, in addition to attenuating the light as a function of wavelength, also applies a dynamic and differential phase shift (between +1 and −1 orders), which will shift the image of the source object on the detector for the wavelength, wavelength band and/or polarization concerned.

Another way of compensating GH errors, according to the principles of the present invention, is referred to as the "digital" or "digital filter" approach. With this approach, rather than modifying the spectrum in the incident and reflected light, a spectral and polarization filter is applied in software after each wavelength, wavelength band and/or polarization is detected separately in space, time or angle in accordance with the principles of the present invention. A single broadband spectrum, or many narrow band spectra, or a combination of broad and narrow band spectra are used to illuminate the substrate. The combined spectrum is then separated into several sub-bands and polarizations that are directed at one or more detectors that sense the position of the substrate and possibly its reflectance as a function of wavelength, polarization. Then the AF position is estimated with a weighted average among the spectral and polarization components, where the weighting (known as a digital filter) is made to reduce the overall variation in GH error across various substrate conditions for a given process (and/or a given imaging optical system). This type of system and method can be used with a fixed optical system with few or no moving parts.

In one version of the digital approach, broadband unpolarized illumination is used in imaging the object (e.g. slits or fringes) to the substrate. The light leaving the substrate is then separated into different polarizations and wavelengths that are then detected separately. The key point here is that the separation is done after reflection from the substrate. In this version of the method, a combination of dichroic and polarization beam splitters can be used to separate the measurements. In another embodiment, gratings can be used to perform the chromatic separation. In another preferred embodiment, the chromatic separation can be performed by a pair of prisms, a first prism that spreads the reflected light as collimated light in angles by wavelengths, and a second prism that is displaced from the first prism along the z axis, and makes the collimated rays at all the wavelengths parallel, so that the wavelengths are spatially separated, but their directions maintained. In either case of gratings, or prisms used to perform the chromatic separation, polarization beam splitters can be used to perform the polarization separation. In another embodiment, the polarization separation can be performed with polarizing elements placed directly in front of the detector elements that receive duplicate images of the of the source object.

In another version of the digital approach, the source object is illuminated by light that contains a plurality of wavelength bands such that each wavelength band is well separated in the far field image of the object. In this case, the different wavelengths can be picked off in the pupil of the relay optics following reflection by the substrate. With the wavelength well separated in the pupil, a set of mirrors or prisms can be used to direct each wavelength band to different detectors. In a preferred embodiment, a set of tilted mirrors is used to translate the image to different areas of a CCD. In this approach, polarization can be separated in the same way, or as is preferred, by a polarizing beams splitter that sends the beam to two separate CCDs.

In yet another version of the digital approach, the source object is illuminated sequentially in time by a plurality wavelength bands and polarizations. In this embodiment, the measurements at each polarization and wavelength band are also made sequentially in time.

In all of the disclosed versions of the invention, it is preferred that source object, that being imaged onto the substrate, and relayed to a detector, comprise a set of sinusoidal fringes produced by two-beam interference. Such fringes can be generated by illuminating a linear grating having twice the desired periodicity, and filtering the far field image such that only the +1 and −1 orders are allowed to reach the detector.

The present invention takes advantage of the fact that the GH error is significantly different across wavelengths and polarizations. Because of this, different spectra have different amounts of GH error for different substrate structures. And measurements made at a plurality of wavelengths and polarizations similarly contain information about those substrate structures.

Thus, the present invention compensates GH errors with or without detailed information about the substrate, without the complexities of ellipsometry (it can be thought of as an approximation or short-cut to ellipsometry), in a manner such that the GH error can be reduced to almost arbitrarily low levels.

Further aspects of the present invention will become apparent from the following detailed description and the accompanying drawings.

DETAILED DESCRIPTION

As described above, the present invention provides a new and useful concept for compensating errors due to the Goos-Hanchen (GH) effect in an autofocus (AF) system. The principles of the present invention are particularly useful in compensating GH errors in a fringe type AF system, and are described herein in connection with such a system. However, from that description, the manner in which the principles of the present invention can be applied to other AF systems (e.g. systems that use slit type detection) will be apparent to those in the art.

Figure 1:
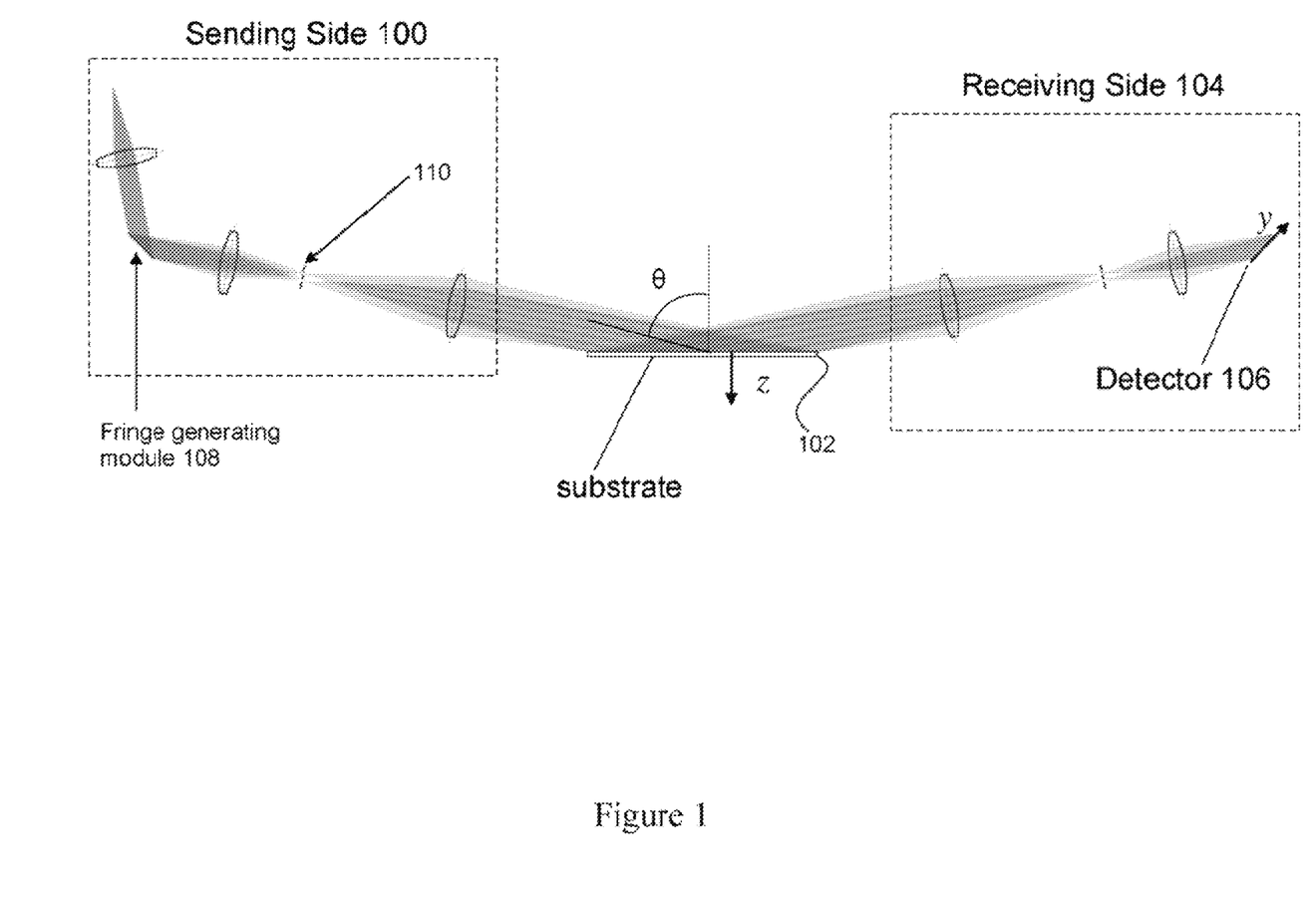
FIG. 1 is a schematic illustration of a fringe type projection system, with which the present invention is particularly useful.

FIG. 1 schematically illustrates the principles of an autofocus (AF) system and method, using fringe projection. The system has a sending side 100, from which light is directed at a substrate 102, and a receiving side 104, wherein light reflected from the substrate is directed to a detector 106. On the sending side 100, the light (e.g. broadband or "white" light) is reflected from a fringe generator 108, filtered by a filter 110 and reflected from the substrate 102. The fringe(s) of the reflected light is (are) detected at the detector 106, and used to determine the initial position of the substrate surface in the z direction. Subsequent operation of the AF system is then used to determine changes in the z position, and those changes may be used to control movement of the stage that supports the substrate in the z direction. The "fringe shift", i.e. the amount by which the fringe is shifted, may be defined by $y = 2 m^2 z \tan \theta$, where z is the z position of the substrate, $\theta$ is the angle of incidence (shown in FIG. 1), m is the magnification between the substrate and detector, and y is the fringe position along the detector (shown in FIG. 1).

There are two (2) basic approaches to the method by which Goos-Hanchen errors may be compensated, according to the principles of the present invention; one is referred to herein as the "analog" approach, and the other is referred to herein as the "digital" or "digital filter" approach.

The analog approach is an extension of the idea that a different spectra produce different amounts of Goos-Hanchen (GH) error for a given surface, and that there is some spectrum that will minimize this error. Therefore to compensate the GH error, the method of the invention provides for adjusting the input spectrum, either by filtering the spectrum (and polarization) of a broad band source, or by varying the amount of light that is allowed to pass from a set of relatively narrow band sources. A related approach, which can still be referred to as an analog approach, is to introduce a wavelength (and polarization) dependent shift to fringes in fringe projection systems (or to the slit images in slit projection systems). This allows the implementation of negative spectral components. In practice a combination of these approaches may be beneficial. In these versions of the analog approach, the average autofocus signal (averaged over all wavelengths) will contain reduced GH error, and has the convenience of using few detector elements relative to the digital method.

In the digital approach, the optical AF signal is divided into spectral (and polarization) components at the detector. This can be done in time by pulsing the sources and alternating/rotating the polarization state (this could also be done to the light after it is incident on the substrate with appropriate chopping and/or switching mechanisms), or by separating the image spatially and sending the different wavelengths (and polarizations) to different detector elements—producing a plurality of AF measurements for a single position on the substrate. Once the plurality optical AF measurements have been made for a single position, they are combined by a weighted sum, where the weightings have been chosen to reduce the dependence on the GH error, much in the same way the spectrum was chosen in the analog approach.

In choosing the weights or the spectra; in order to effectively reduce the GH error, a set of weights or spectra shapes that achieve this goal must be found, and there are several possible approaches. For example, one way to determine the GH error as a function of the spectra or weights is by simulation, and then determining the best spectra or set of weights by some sort of optimization—e.g. simulated annealing, or damped least squares. Another approach, is to make a set of chromatic and polarization separated optical AF measurements on the target surface, and then also measure the surface by some other method that does not have GH errors (like an air-gauge, or touch profilometer) and then find the set of weights that reduces the GH error. This approach is easily amenable to a least squares solution and one skilled in the art will easily see that.

Another way to characterize the digital approach is that each wavelength (and polarization) is used to measure the z position of the substrate. This gives a set of measured z positions. Then, the weighted average (set of a and b coefficients) are applied to the set of z positions to give a single, final, corrected measurement of the substrate z position. In order to know the coefficients a, b, the AF system must be calibrated for a given substrate type. This can be done in at least 2 ways:

a) Use a physical sensor (air gauge, etc) to measure the height at some set of positions on the substrate and compare this with the results from the optical autofocus system. The air gauge or other physical sensor can't be used for every substrate because it is much slower and has a hard time measuring many points. This is done once per process, establishing the set of {a, b} b) Print a test substrate for a given process and use the result of the printing (which used the data from the optical AF to establish the substrate at the right z height during printing) to determine the error of the optical AF, and use this to determine the set of {a, b}.

In the digital approach, it is possible to use other information (such as the amount of reflected light, for example) to sub-classify different regions on the substrate. Say half the substrate has copper (process A) and the other half has no copper (process B). There could be 2 sets of coefficients {a, b}, that could be preferentially applied depending on which region is being measured.

Also, in the digital approach, the light reflected by the substrate is used to determine changes in the z position of the substrate by applying a weighting average to the set of z measurements at the different wavelengths ($\lambda$'s) and polarizations (e.g. s and p polarizations), and using the weighting average to make corrections that account for the Goos-Hanchen effect. Moreover, the weighting average is produced by a linear least squares regression estimate of the coefficients of the first order position of the substrate, preferably according to the following formula $$Z_j = a_0 + \sum_{n=1}^{N}\sum_{v=s,p} a_{k,v} z_{j,n,v} + \sum_{m=1}^{M}\sum_{v=s,p} b_{k,v} r_{j,m,v}$$

where
Zj is the substrate height at position j on the substrate
$a_o$ is a DC offset value
$a_k$ is the set of coefficients for the $z_j$(lambda) measurements, where there is a different j for each wavelength $$\sum_{v=s,p}$$

This is a sum over the s and p polarization measurements
M is the number of wavelength bands
$r_{j,m,v}$ is the reflectance at
   $j^{th}$ position
   $m^{th}$ wavelength band (or sub-spectrum)
   $v^{th}$ polarization
$z_{j,n,v}$ is the z height at
   $j^{th}$ position
   $n^{th}$ wavelength band
   $v^{th}$ polarization
$b_k$ is the set of coefficients for the reflectance measurements of the substrate, $r_j$ (lambda). The same data collected and used to measure z will also be used to calculate wavelength dependent values for r, the reflectance. The set of b's are the weighting coefficients for making a correction using this data.

For a and b, the v subscript is for the two polarization states (s and p).

By comparison, the analog approach would use the same type of calibration for determining the set of {a, b}, but it would be really hard to have spatially varying sets of coefficients (say, 2 sets for process A and B). The implementation of the filter would be done by attenuating the light at the various wavelengths and polarizations using a mechanical shutter, or filter. Then, the detector would measure z only once, and that measured z would be the result of applying the {a,b} coefficients directly on the light, rather than on the digital, calculated versions of z. The potential advantage of the analog method is that the data collected could be much less and the corrected z measurement could be determined very quickly.

Figure 2A:
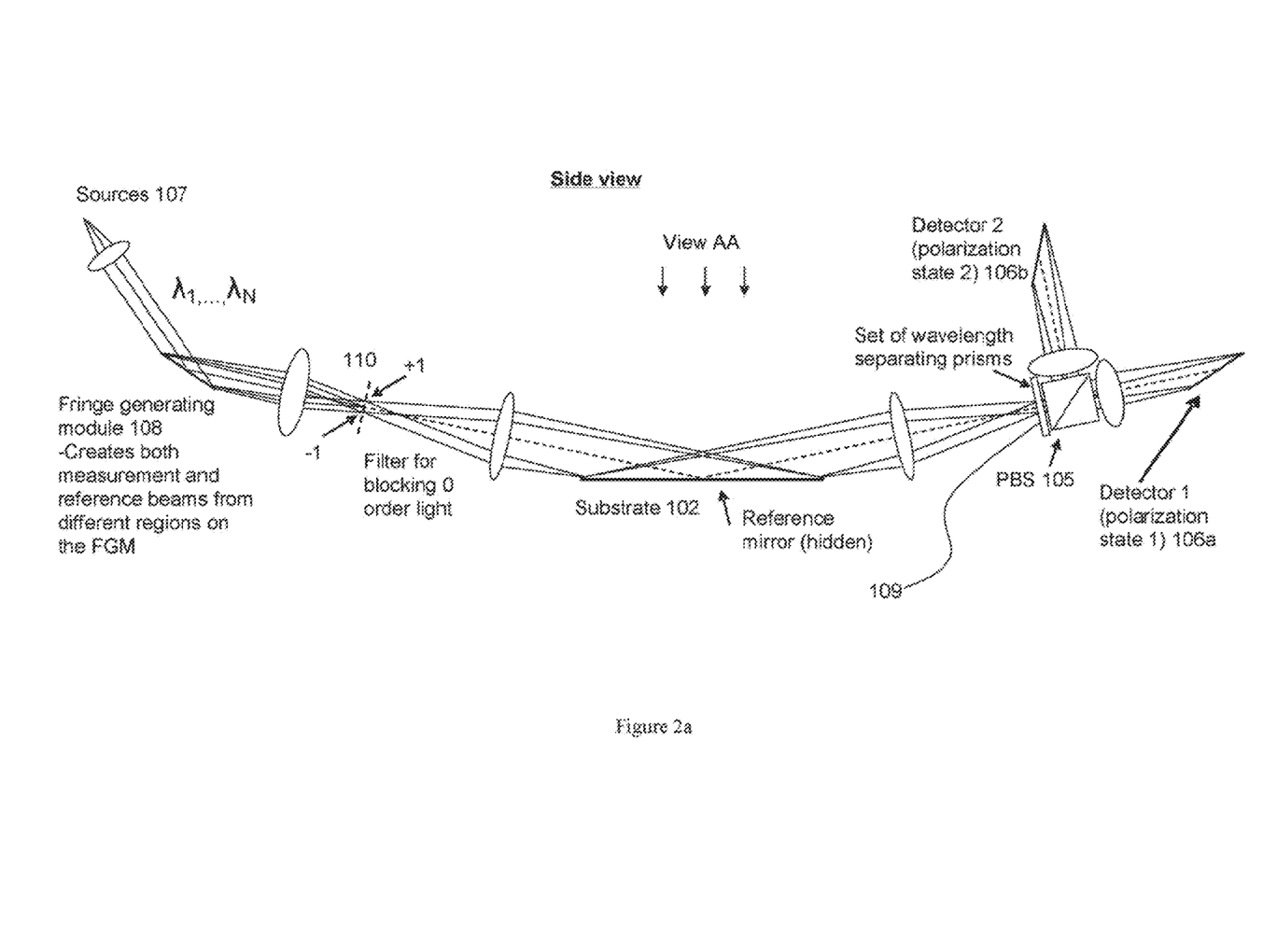
FIGS. 2a and 2b are schematic illustrations of one way of compensating the GH effect, in accordance with the principles of the present invention.
Figure 2B:
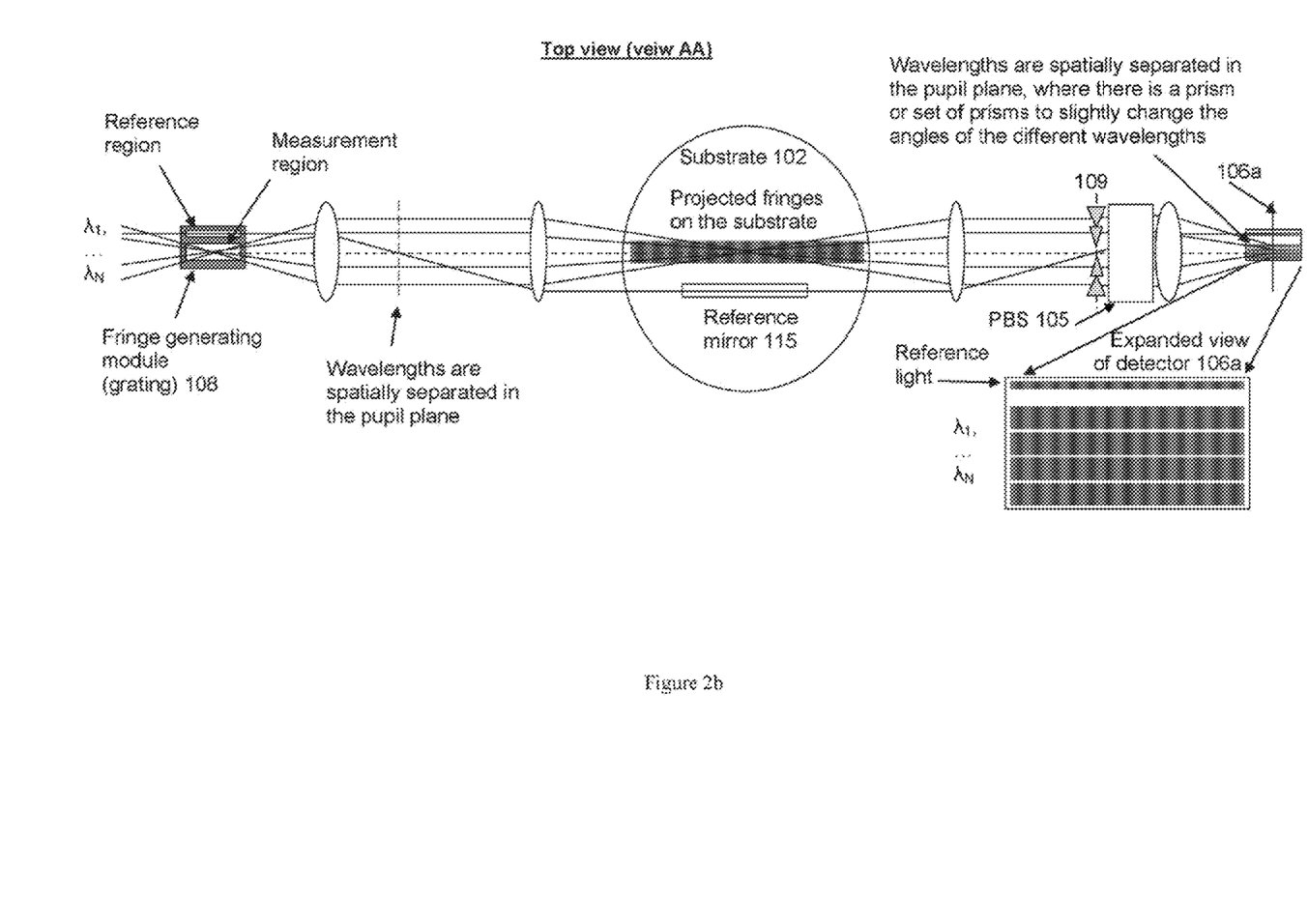

FIGS. 2a and 2b schematically illustrate one version of providing an AF system and method that compensates errors due to the GH effect, which is particularly useful with the digital approach described herein. In the system and method of FIGS. 2a and 2b, the light is directed at the substrate 102 at a plurality of wavelengths ($\lambda$'s), the light at the plurality of wavelengths is reflected from the substrate (and from a reference mirror) and broken into different polarizations, and then detected. In this version of the method, separate light sources 107 of finite spectral width are incident on the substrate 102 (and on a reference mirror 115) at different angles such that they can be separated in angle space. The light from the sources is reflected from a fringe generating grating forming part of a fringe generating module 108 (and also from a reference region of the fringe generating module), and directed through a filter 110 before it is reflected from the substrate 102 and the reference mirror 115. The reflected light at the different wavelengths is spatially separated by prisms 109, and then separated by polarization by means of a polarization beam splitter PBS 105. Thus, reflected light at the different wavelengths and polarizations is directed to respective detectors 106a, 106b.

Figure 3A:
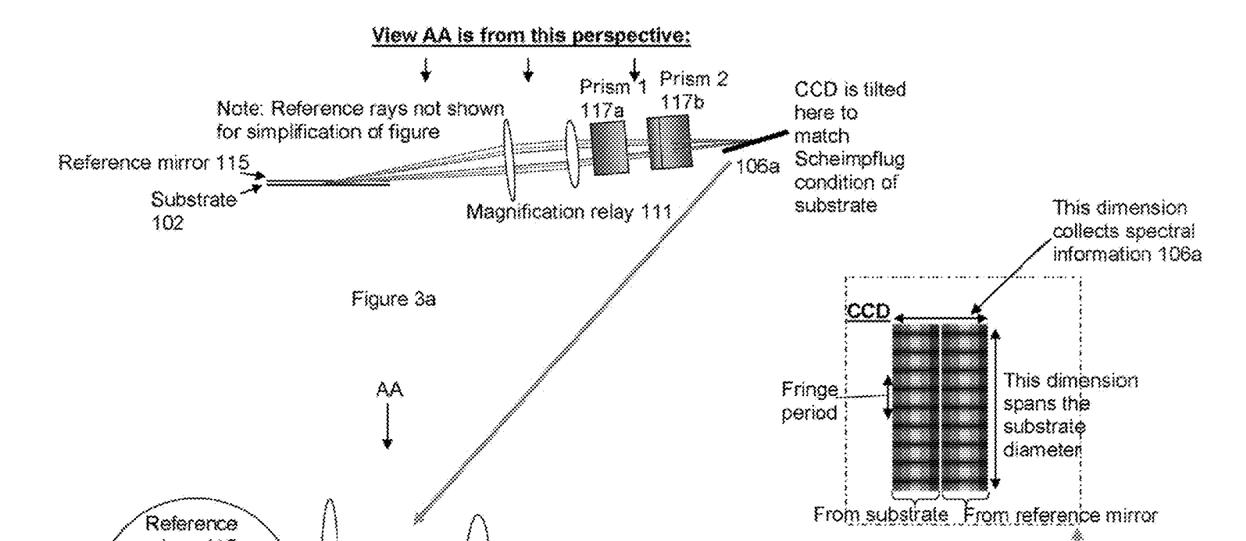
FIGS. 3a and 3b are schematic illustrations of additional aspects of compensating GH errors in an autofocus system, in accordance with the principles of the present invention.
Figure 3B:
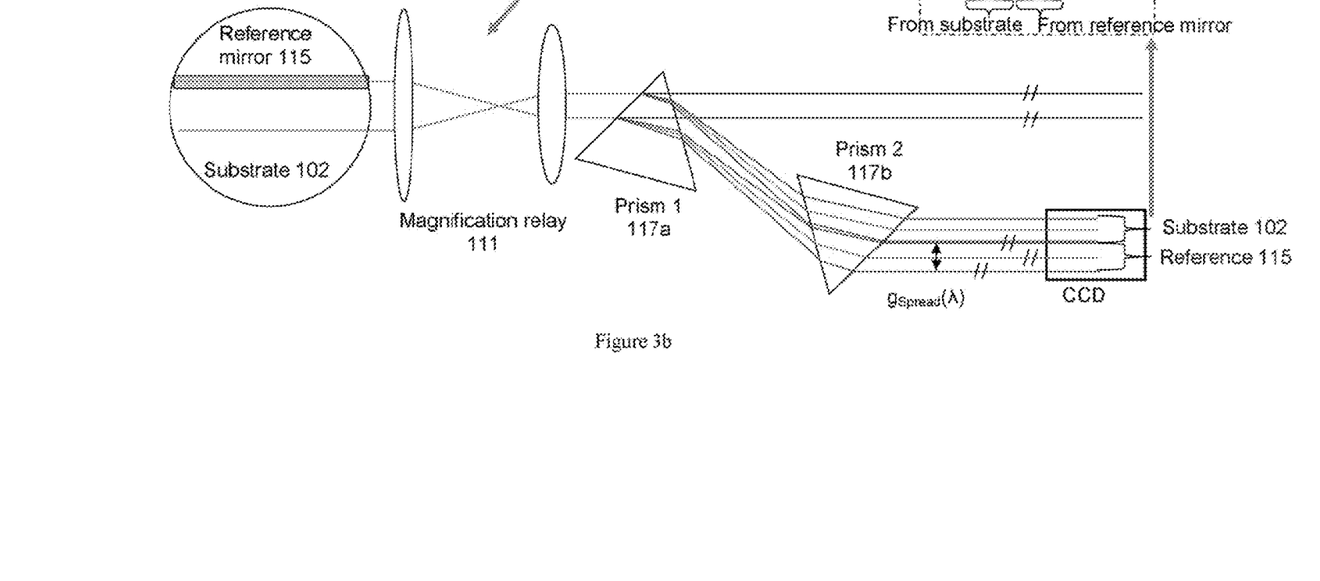
Figure 4:
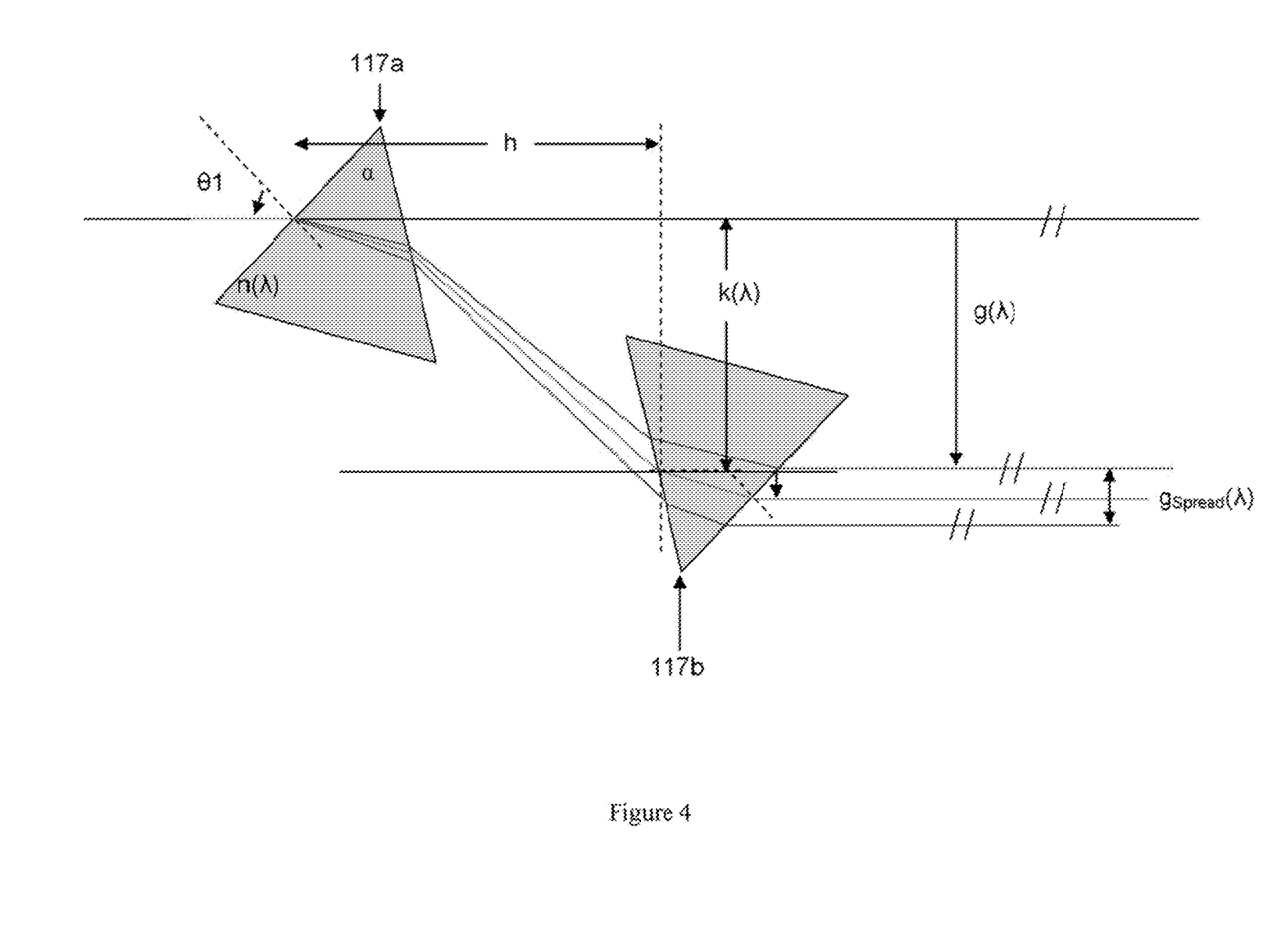
FIG. 4 is an illustration of a pair of prisms that can be used on the detection side of a system in practicing the principles of the present invention.

In another version of an autofocus system and method, according to the principles of the present invention, which is also particularly useful with the digital approach described herein, and shown schematically in FIGS. 3a, 3b, and 4, broadband light (or "white") light from a broadband source is directed at a substrate 102 (and also at a reference mirror 115), (through a fringe generating module 108 and a filter 110, that are similar to the prior embodiment and therefore not shown). Broadband light reflected light from the substrate 102 and the reference mirror 115 is then magnified (e.g. by a magnification relay 111), broken into different polarizations and wavelengths that are then detected. In this version of the method, it is preferred that the broadband light reflected from the substrate (and the reference mirror) is refracted by a pair of prisms 117a, 117b, a first prism 117a that spreads the reflected light as collimated light in angles by wavelengths, and a second prism 117b that is displaced from the first prism along the z axis, and makes the collimated rays at all the wavelengths parallel, so that the wavelengths are spatially separated. The light is further separated by polarization, by polarization beam splitters similar to 105 (FIG. 2a), and detected by detectors 106a, 106b.

In yet another version of an autofocus system and method, according to the principles of the present invention, which is also particularly useful with the digital approach described herein, the system would be set up in a manner similar to that shown in FIGS. 2a, 2b, but light that is directed at the substrate 102 comprises light from an illumination source that produces light sequentially at a plurality of wavelengths and a plurality of polarizations, and light at the plurality wavelengths and polarizations is detected sequentially. In this version, there would not be a need for the plurality of prisms 109 shown in FIGS. 2a, 2b.

In all of the disclosed versions of the invention, it is preferred that source object, that being imaged onto the substrate, and relayed to a detector, comprise a set of sinusoidal fringes produced by two-beam interference. Such fringes can be generated by illuminating a linear grating having twice the desired periodicity, and filtering the far field image such that only the +1 and −1 orders are allowed to reach the detector.

Thus, the basic concept of the present invention corrects for GH error in an AF system and method, by detecting light reflected from the substrate at different wavelengths and different polarizations, and using the detected light to compensate GH error. The principles of the present invention can be applied to either slit detection or fringe detection, but fringe detection is currently preferred. However, from this description, the manner in which the principles of the invention can be practiced with slit detection will be apparent to those in the art.

Also, in applying the principles of the present invention to an AF system and method, it should be noted that light directed at the substrate is preferably in a spectral range of 400 nm to 1000 nm so that it can work with the most commonly available glasses and detectors, but in principle can be any range of wavelengths that do not damage or alter the surface under investigation. The manner in which the light is directed at the substrate at a plurality of wavelengths and polarizations can take a number of forms, such as a single broadband light source that is filtered to produce the different wavelengths and different polarizations, or a plurality of light sources that produce light in narrow bands, and at different polarizations. The light at the plurality of wavelengths and polarizations is directed at the substrate (and the reference mirror), and reflected light from the substrate (and the reference mirror), at the plurality of wavelengths and polarizations, is directed to one or more detectors. The detected light is used to determine changes in the z position of the substrate being imaged. Preferably, the invention contemplates separate detection for each wavelength and each polarization. Moreover, the detector(s) can also measure the reflectance of the substrate, which is useful with the digital filter aspect of this invention, described further below.

The "analog" approach uses a broadband light source, and filters (e.g. dynamic filters or custom filters), or a number of multiplexed broadband or narrowband sources, to modify the spectrum (both wavelength and polarization) so that the variation of GH error is minimized across various substrate patterns. Thus, a broad band illuminating spectrum is filtered with a dynamic filter, or with a custom interference filter, to produce light at different wavelengths and polarizations in the light directed at the substrate and/or the light reflected from the substrate, and each of those different wavelengths and polarizations is detected simultaneously. Each sub-band and polarization is biased by the measurement system, so that, for example, individual wavelength bands and polarizations contain more or less power relative to the others and may also overestimate or underestimate the substrate position so that the final measurement has reduced sensitivity to GH shifts.

With the "digital filter" approach, a spectrum filter is applied in software. On the "sending" side of the substrate (i.e. from which light is directed at the substrate), the light is produced by a broadband source (that is filtered, e.g. by a turret filter) or several discrete light band sources, to direct light at the substrate at different wavelengths and at the different polarization (i.e. s and p polarizations) and possibly different angles of incidence. On the "receiving" side of the substrate (i.e. which receives the reflected light from the substrate) reflected light at the different wavelengths and polarizations is directed at one or more detectors, and the light at the different wavelengths and polarizations is separately measured at the detectors. The information from the detectors can then be used to determine variations of the z position of the substrate. The detector(s) can take various forms, e.g. CCD (charged couple device), individual slit detectors, etc., which would collect data so that the phase of the projected fringes can be calculated and the substrate height can be measured. Prisms or gratings are used to separate the fringes into finite wavelength bands, e.g. corresponding to pixel columns on the CCD. This allows for the use of a digital filter approach, as described herein.

The digital filter approach can be practiced with a serial or parallel approach, in terms of the way light is handled at the sending and receiving sides of the substrate. The "serial" approach provides a single detector that is sensitive to multiple wavelengths and polarizations on the receiving side, and a sending side that is switched between wavelengths and polarizations sequentially in time. The serial approach allows for switching between sources at discrete bands, or providing filters with broadband sources (e.g. turret type filters), or by switching between different sources having different spectra. If filters are used they can be on the sending and/or the receiving side of the substrate. With the "parallel approach", all wavelengths and polarizations are projected simultaneously at the substrate; the wavelengths and/or polarizations may be split at the receiving side of the substrate and directed to multiple detectors. Then the AF position is estimated with a weighted average among the spectral and polarization components, where the weighting (analogous to a digital filter) is made to reduce the overall variation in GH error across various substrate conditions for a given process.

As specifically illustrated in FIGS. 3a, 3b and 4, where a broadband source is reflected from the substrate, in order to separate the wavelengths, a pair of prisms is used (117a, 117b). The first prism (117a) spreads the collimated light out in angle by wavelength. The second prism (117b) makes rays from all wavelengths parallel again, but since the second prism is displaced along the z-axis from the first prism, the colors have been spatially separated. This light is then incident on the detector(s).

With a system and method using the principles of the present invention, because the GH error is strongly dependent on wavelength, a small change in the spectrum of a broad-band source can have a noticeable effect on the error. Thus, the principles of the present invention contemplate using a spectrum where the GH error is minimized, modifying the illuminating spectrum with some sort of dynamic filter, measuring the slits or fringes at several wavelength bands and apply the spectrum in software as a digital filter.

The digital filter approach is particularly attractive (and is therefore currently preferred) because phase and reflectivity information can be generated, as well as irradiance (light intensity), all of which are related to changes in the z-position of the substrate and can easily be incorporated into a digital filter.

A system and method that practices the principles of the present invention can be thought of as a short-cut to ellipsometry where, instead of a priori knowledge, measurements from a sensor that is relatively immune to the GH effect can be used to determine the filter that best matches the measured z-position. Moreover, it may be possible to use the optical sensor data from several substrates to find a filter that minimizes the variation, possibly allowing for low order deformations of the substrate surface. In either case, the method could be largely automated.

With the digital approach, the method of finding the spectral filter is currently a linear least squares estimate of the coefficients of the first order position of the substrate as function of wavelength band and polarization, but it is recognized that there will be other approaches that can be used, and that higher order regression models involving other measurable quantities like reflectance can be included in the filter.

In one preferred embodiment of the digital filter approach, the optimal filter is calculated from a set of measured substrate heights $z_j(k_v)$ where j (from 1 to N) indicates the location of the measurement on the substrate, $k_v$ indicates the wavelength band k (from 1 to M) and polarization state v (e.g., either s, or p). At each of these locations, there is also a known substrate height $Z_j$, which may be measured by an independent system that is relatively immune to the GH effects. Given this notation, we desire an estimate of the known height $Z_j$ in terms of the spectrally measured heights $z_j(k_v)$. The simplest solution form is a linear combination of the measured heights, $$Z_j = a_0 + \sum_{k=1}^{M} \sum_{v=s,p} a_{kv} z_j(\lambda_{kv}).$$

One approach for determining the coefficients is linear least squares regression using the following regression model (which is described in paragraph 0028).

$$Z_j = a_0 + \sum_{n=1}^{N} \sum_{v=s,p} a_{k,v} z_{j,n,v} + \sum_{m=1}^{M} \sum_{v=s,p} b_{k,v} r_{j,m,v}.$$

where
Zj is the substrate height at position j on the substrate
$a_o$ is a DC offset value
$a_k$ is the set of coefficients for the $z_j$(lambda) measurements, where there is a different j for each wavelength $$\sum_{v=s,p}$$

This is a sum over the s and p polarization measurements
M is the number of wavelength bands
$r_{j,m,v}$ is the reflectance at
  $j^{th}$ position
  $m^{th}$ wavelength band (or sub-spectrum)
  $v^{th}$ polarization
$z_{j,n,v}$ is the z height at
  $j^{th}$ position
  $n^{th}$ wavelength band
  $v^{th}$ polarization
$b_k$ is the set of coefficients for the reflectance measurements of the substrate, $r_j$(lambda). The same data collected and used to measure z will also be used to calculate wavelength dependent values for r, the reflectance. The set of b's are the weighting coefficients for making a correction using this data.

For a and b, the v subscript is for the two polarization states (s and p).

In an extension of this approach, nonlinear combinations of the various measurements may be included in the model. For example, the square of each z-measurement $z_j(k_v)$, or cross terms like $z_j(k_v) z_j(l_t)$. Similarly, cross terms between reflectance measurements and cross terms between z and r can be used to make the correction, to any order deemed useful by the usual techniques of regression analysis or by careful analysis of the ellipsometric relationships.

A further extension of this approach could include measurements of substrate height and reflectance at multiple angles of incidence and/or substrate orientation (i.e. clocking).

Also, one could use a nonlinear regression, for example with polynomial basis as follows:

$$Z_j = a_0 + \sum_{n=1}^{N} \sum_{q=1}^{Q} \sum_{v=s,p} a_{k,v} z_{j,n,v}^q + \sum_{m=1}^{M} \sum_{v=1}^{T} \sum_{v=s,p} b_{k,v} r_{j,m,v}^t$$

It is also preferred that the projected pattern (either slits or fringes) at all wavelengths have the same period and phase, and that all of the wavelengths are looked at simultaneously, or separated with a prism/grating such that each band corresponds to one region of an area detector (e.g., a charge coupled device (CCD)). Those principles would utilize, e.g., a mirror array placed conjugate to the substrate.

Thus, the foregoing description provides several new and useful ways of compensating for errors due to the Goos-Hanchen effect in an optical autofocus system and method that uses light reflected from a substrate to determine changes in the z position of the substrate. The correction is performed through the use of reflected light from the substrate at a plurality of wavelengths and polarizations that is detected and used to make corrections to the z position of the substrate that compensate for the errors due to the Goos-Hanchen effect. From the foregoing description, other ways of compensating for errors due to the Goos-Hanchen effect in an autofocus system and method, using the principles of the present invention, will become apparent to those in the art.

What is claimed is:

1. A surface position measuring apparatus comprising:
   a light-sending optical system configured to deliver a measuring beam on a measuring area on a substrate at an oblique angle to form a measuring pattern on the measuring area;
   a light-receiving optical system configured to receive light, from the measuring beam, that has interacted with the measuring area, from the measuring area as a first beam of light;
   a spectroscope unit disposed in optical communication with the light-receiving optical system and configured to separate said first beam of light into spectral components propagating along a separating direction, the separating direction being transverse to a longitudinal direction of the measuring pattern; and
   an optical detector system disposed to acquire said spectral components to form a spectral image of the measuring pattern,
   wherein the spectroscope unit includes an optical filter configured to modify at least one of a spectrum, state of polarization, phase, and irradiance of at least one of said spectral components to compensate an error contributed to said spectral image by a Goos-Hanchen shift experienced by the measuring beam at the substrate.

2. The position measuring apparatus of claim 1, wherein said pattern has a spatial period along the longitudinal direction.

3. The position measuring apparatus of claim 1, further comprising a polarization beam splitter disposed across said first beam of light to separate the first beam of light into beam components having different polarization states.

4. The position measuring apparatus of claim 3, wherein the polarization beam splitter is configured to separate the first beam of light into polarization components that propagate along a direction transverse to the separating direction.

5. The position measuring apparatus of claim 1, wherein the spectroscope unit is disposed between the measuring area and the detector.

6. The position measuring apparatus of claim 1, wherein the light-sending optical system includes an optical objective positioned across the measurement beam configured to transform said measurement beam upon transmission therethrough into a first measurement beams and a second measurement beam that form respectively-corresponding first and second measuring patterns on the measuring area.

7. The position measuring apparatus of claim 6,
   wherein the light-receiving optical system is configured to guide light from the first measuring beam, that has interacted with the measuring area, as a first image beam to form an image of the first measuring pattern on a first detecting surface of the optical detector system;
   to guide light from the second measuring beam, that has interacted with the measuring area, as a second image beam to form an image of the second measuring pattern on a second detecting surface of the optical detector system;
   wherein the first and second detecting surfaces are different from one another.

8. The position measuring apparatus of claim 7, wherein the spectroscope unit is structured to separate the first image beam into corresponding spectral components to form a spectral image of the first measuring pattern, on the first detecting surface.

9. The position measuring apparatus of claim 8, wherein the detector which detects the spectral image of the first measuring beam on the first detecting surface and the second measuring beam on the second detecting surface.

10. The position measuring apparatus of claim 7,
    wherein said spectroscope unit is further configured to introduce a dynamic differential phase shift between said first and second image beams to cause a spatial offset between said first and second image beams.

11. The position measuring apparatus of claim 6, wherein the first measuring pattern has a spatial period along the longitudinal direction.

12. The position measuring apparatus of claim 7, wherein a detecting surface of the optical detection system is tilted with respect to an optical axis of a beam of light from the first and second image beams.

13. The position measuring apparatus of claim 7, further comprising a polarization beam splitter disposed across said first and second image beams to separate the first and second image beams of light into respectively-corresponding beam components having different polarization states.

14. The position measuring apparatus of claim 9, further comprising a reference member cooperated with the substrate, the reference member disposed to redirect light forming the second image beam from the second measurement beam to the light-receiving optical system.

15. A surface position measuring method comprising:
    obliquely delivering a measuring beam of light to a measuring area on a substrate;
    forming a measuring pattern on the measuring area with said measuring beam of light;
    at the substrate, redirecting light from the measuring beam that has interacted with the substrate to form an first beam;
    separating the first beam into spectral components along a separating direction, the separating direction being transverse to a longitudinal direction of the measuring pattern;
    creating a polychromatic image of the measuring pattern on a detecting surface of an optical detection system, wherein said creating includes optically filtering said first beam to modify at least one of a spectrum, state of polarization, phase, and irradiance of said first beam to compensate and error contributed to the polychromatic image by a Goos-Hanchen shift experienced by the measuring beam of light at said substrate; and
    acquiring light from said polychromatic image with the optical detection system.

16. The position measuring method of claim 15, wherein the forming includes forming the measuring pattern having a spatial period along the longitudinal direction.

17. The position measuring method of claim 15, further comprising separating the first beam into beam portions each of which has a different state of polarization.

18. The position measuring method of claim 17, wherein the separating includes separating the first beam into said beam portions that propagate along a direction transverse to the longitudinal direction.

19. The position measuring method of claim 15, wherein said optically filtering includes compensating an average error cause by said Goos-Hanchen shift, said average error defined with averaging over wavelengths and polarization states of light delivered to the detecting surface.

20. The position measuring method of claim 15, further comprising acquiring a distribution of irradiance across the detecting surface, with said optical detection system, only once to determine a compensation for said error.

21. The position measuring method of claim 15, further comprising reflecting light from the measuring beam at a reference reflector disposed in cooperation with the substrate.

22. The position measuring apparatus according to claim 1, configured as an autofocus (AF) system.

* * * * *